United States Patent [19]

Shaw

[11] 4,207,896

[45] Jun. 17, 1980

[54] SURGICAL INSTRUMENT HAVING SELF-REGULATING DIELECTRIC HEATING OF ITS CUTTING EDGE

[76] Inventor: Robert F. Shaw, 50 St. Germain, San Francisco, Calif. 94114

[21] Appl. No.: 558,333

[22] Filed: Mar. 14, 1975

Related U.S. Application Data

[63] Continuation-in-part of Ser. No. 534,756, Dec. 2, 1974, Pat. No. 4,089,336, which is a continuation of Ser. No. 63,645, Aug. 13, 1970, abandoned, which is a continuation of Ser. No. 681,737, Nov. 9, 1967, abandoned.

[51] Int. Cl.² .................. A61B 17/32; A61N 3/00
[52] U.S. Cl. .................... 128/303.1; 30/140; 219/233
[58] Field of Search .......... 30/140; 128/303.1, 303.13, 128/303.14; 219/10.49, 10.57, 221, 223, 227, 228, 229, 230, 231, 233, 241

[56] References Cited

U.S. PATENT DOCUMENTS

| | | | |
|---|---|---|---|
| 1,805,904 | 5/1931 | Carpenter | 128/303.14 |
| 1,975,437 | 10/1934 | Sorrel | 219/10.49 |
| 2,863,036 | 12/1958 | Mitchell et al. | 30/140 |
| 3,024,342 | 3/1962 | Birnbach et al. | 30/140 |
| 3,489,884 | 1/1970 | Waseleski, Jr. | 219/241 UX |
| 3,515,837 | 6/1970 | Ando | 219/10.49 |
| 3,524,966 | 8/1970 | Ando | 219/10.49 X |
| 3,768,482 | 10/1973 | Shaw | 128/303.1 |

FOREIGN PATENT DOCUMENTS

1157711 7/1969 United Kingdom .................. 219/10.49

OTHER PUBLICATIONS

Murakami, K., "The Characteristics of Ferrite Cores with Low Curie Temperature", in IEEE Trans. on Magnetics, Jun. 1965, pp. 96-100.
Bennett, Edward, "The Proximity Effect:Its Application etc.", in Trans. AIEE, 51: 621-627, 1932.
Bennett, Edward, "Concentration of Heating Currents", in Electrical Engineering, Aug. 1932, pp. 559-562.

*Primary Examiner*—Robert W. Michell
*Assistant Examiner*—Michael H. Thaler
*Attorney, Agent, or Firm*—Lyon & Lyon

[57] ABSTRACT

The cutting edge of a scalpel blade is heated to an elevated preselected constant operating temperature for cutting tissue with simultaneous hemostasis by dielectric heating of the internal structure of the blade in the region along the cutting edge. Selective heating of regions of the cutting edge that are locally cooled by contact with tissues during surgical cutting is provided for by constructing the heating elements of the blade of ferroelectric materials that have a Curie point in the operating temperature range and that provide large increases in loss factor (the product of relative dielectric constant times the ratio of loss current to charging current) for temperature decrements below the Curie point.

4 Claims, 4 Drawing Figures

SURGICAL INSTRUMENT HAVING SELF-REGULATING DIELECTRIC HEATING OF ITS CUTTING EDGE

RELATED APPLICATIONS

This application is a continuation-in-part of U.S. patent application Ser. No. 534,756 filed Dec. 2, 1974, now Pat. No. 4,084,336, which is a continuation of U.S. patent application Ser. No. 63,645 filed Aug. 13, 1970, now abandoned, which is a continuation of U.S. patent application Ser. No. 681,737 filed Nov. 9, 1967, now abandoned.

BACKGROUND OF THE INVENTION

The control of bleeding during surgery accounts for a major portion of the total time involved in an operation. The bleeding that occurs from the plethora of small blood vessels that pervade all tissues whenever tissues are incised obscures the surgeon's vision, reduces his precision, and often dictates slow and elaborate procedures in surgical operations. It is well known to heat the tissues to minimize bleeding from incisions, and surgical scalpels which are designed to elevate tissue temperatures and minimize bleeding are also well known. One such scalpel transmits high frequency, high energy sparks from a small electrode held in the surgeon's hand to the tissues, where they are converted to heat. Typically, substantial electrical currents pass through the patient's body to a large electrode beneath the patient, which completes the electrical circuit. Discharge of sparks and temperature conversion in the tissue are poorly controlled in distribution and intensity, and erratic muscular contractions in the patient are produced so that this apparatus cannot be used to perform precise surgery. Further, apparatus of this type frequently produce severe tissue damage and debris in the form of charred and dead tissue, which materially interfere with wound healing.

Another well-known surgical scalpel employs a blade with a resistive heating element which cuts the tissue and provides simultaneous hemostasis. Although these resistive elements can be readily brought to a suitably high and constant temperature in air prior to contacting tissues, as soon as portions of the blade came in contact with tissues, they are rapidly cooled. During surgery, non-predictable and continuously varying portions of the blade contact the tissues as they are being cut. As the blade cools, the tissue cutting and hemostasis become markedly less effective and tissue tends to adhere to the blade. If additional power is applied by conventional means to counteract this cooling, this additional power is selectively delivered to the uncooled portions of the blade, frequently resulting in excessive temperatures which may result in tissue damage and blade destruction. This results from the fact that in certain known resistively heated scalpels, the heating is a function of the current squared times the resistance ($I^2R$). In conventional metallic blades of this type, the higher the temperature of any blade portion, the greater its electrical resistance, and consequently the greater the incremental heating resulting from incremental power input.

It is generally recognized that to seal tissues and effect hemostasis it is desirable to operate at a temperature between 300° C. and 1000° C. And for reasons noted above, it is desirable that electrothermal hemostatic surgical cutting instruments include a mechanism by which power is selectively delivered to those portions of the blade that are cooled by tissue contact so that the cutting edge may be maintained at a substantially uniform operating temperature within the desired optimal range. Recently, hemostatic scalpels have been described (see, for example, U.S. Pat. Nos. 3,768,482 and 3,826,263) in which the temperature-controlling mechanisms include resistive heating elements disposed on the surface of the scalpel blade. However, such instruments require precision in fabricating the dimensions of the heating elements to obtain the desired resistances. And such resistive heating elements may be subjected to variations in resistance during sue, as tissue juices and proteins become deposited upon the surface of the blade.

SUMMARY OF THE INVENTION

The present invention provides a surgical cutting instrument in which the cutting portion of the blade is brought to an elevated temperature by dielectric heating of a scalpel constructed of a nonconducting material. Dielectric heating depends on the heat generated by dipole rotation in a dielectric material caused by an alternating electric field.

All materials can be characterized from an electromagnetic consideration with respect to two parameters, namely, the magnetic permeability $\mu$, and the dielectric constant $\epsilon$. Most dielectric materials are nonmagnetic and the permeability is equal to that of free space. Therefore, the controlling parameter in such materials is the dielectric constant, which may be very large relative to free space. To incorporate both a loss current and a charging current, the dielectric constant of a material is generally written in complex form $\epsilon = \epsilon' - j\epsilon''$ where $\epsilon'$ is the real dielectric constant and $\epsilon''$ is the loss factor. The dielectric constant is also often written in relative form $k = k' - jk''$ where $k = \epsilon/\epsilon_o$ and $\epsilon_o$ is the constant of free space.

The power generated in a dielectric is given by $$p = 0.55\,(10^{-12})\,E^2 f k' \tan\delta,$$

in watts/cm$^3$, where E is the electric field in volts per centimeter, f is the frequency in hertz, k' is the relative dielectric constant, and $\tan\delta$ is the ratio of loss current to charging current or $k''/k'$. The power generated in a dielectric is therefore dependent upon the voltage applied to it, the frequency, and the complex dielectric constant of the material.

In the present invention, the tissue-cutting edge of a blade-shaped structure including a dielectric element is heated by the application thereto of a high frequency electrical signal. The electrodes are disposed on the surface of the dielectric element in a manner which establishes a high frequency electric field within the element in a region thereof near the tissue-cutting edge.

Further, selective heating of those portions of the cutting edge that are cooled by tissue contact in order to maintain cutting temperature sufficiently constant (i.e., temperature self-regulation) may be accomplished by fabricating the element of a dielectric material in which the loss factor k'' (i.e., the product of the relative dielectric and the tan $\delta$ [ratio of loss current to charging current, or $K''/k'$]) increases with decreasing temperature. Since each local region of the dielectrically heated material is directly affected by the high frequency electric field, each local region may have its operating temperatures regulated independently of the operating temperatures of adjacent regions. Thus, even in the presence of unpredictable and substantial variations in cooling of the various regions of the heated edge resulting from the edge being manipulated to cut tissues, the heated tissue-cutting edge can be maintained within a suitably constant temperature range.

Ferroelectric materials are examples of dielectrics that have this property near their Curie points. The Curie point of a ferroelectric material is the temperature at which, from an electro-magnetic standpoint, the real dielectric constant experiences a sharp peak and the loss tangent experiences a sharp increase with decreasing temperature. FIG. 3 shows these properties for the ferroelectric barium titanate. It can be seen that there is approximately a 5 to 1 increase in k″ (K′ ×x tan δ) as the temperature drops from 170° C. to 120° C. Therefore, if this material were used to heat the cutting edge of a scalpel blade in accordance with the present invention, and if a constant frequency and voltage were assumed, there would be a 5 to 1 heating increase as the temperature dropped from 170° C. to 120° C. To obtain self-regulation in the 300° C. to 1000° C. range, as is desirable in surgical procedures, it is desirable to have a material with a Curie point within this latter temperature range. There are ferroelectric materials available with a wide range of Curie points. FIG. 4 shows the effect on the real dielectric constant of the addition of lead titanate to barium titanate. The Curie point is moved upward in temperature as the percentage of lead titanate increases. Lead zirconate titanate is an example of a commercially available material with a Curie point in the 400° C. range.

The ferroelectric materials, in addition to having a Curie point that dielectric materials in general do not possess, have large values of k′. This permits generating the desired power in the small volume of material that is present in the scalpel at voltages that are attainable with standard oscillators and that are small enough to prevent breakdown in small diameter coaxial transmission lines. The following tabulation illustrates the difference in power generated within the volume that is typically to be expected between the electrodes on a scalpel blade. Two dielectrics are illustrated, one a ferroelectric and one a more conventional dielectric such as glass.

| Dielectric Constant, k′ - jk″ | Frequency, Hertz | Volts/cm | Watts in 0.01 cm³ |
|---|---|---|---|
| 4-j 0.01 | 4(10⁷) | 2(10³) | 10⁻² |
| 1700-j 34 | 4(10⁷) | 2(10³) | 30 |

DESCRIPTION OF THE PREFERRED EMBODIMENT

Figure 1:
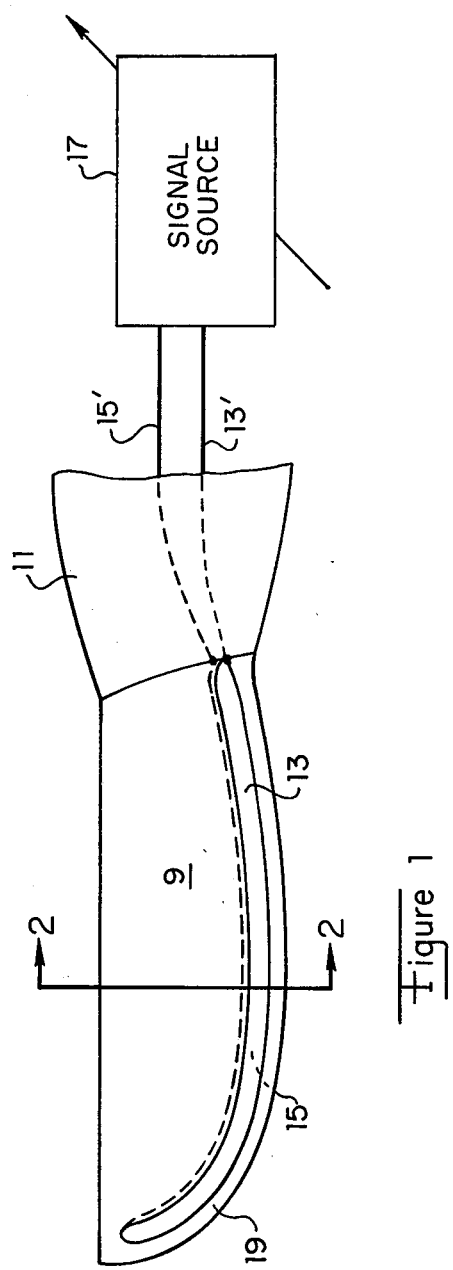
FIG. 1 is a partial side view of a surgical cutting instrument according to one embodiment of the present invention.
Figure 3:
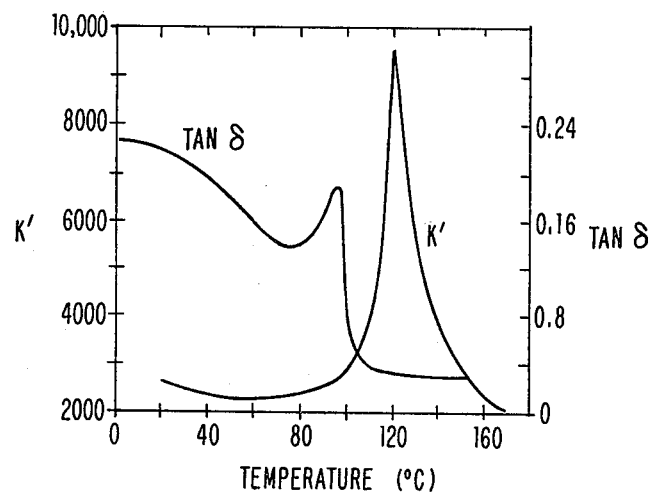
FIG. 3 is a graph showing the temperature dependence of dielectric constant and loss tangent of barium titanate ceramic.
Figure 4:
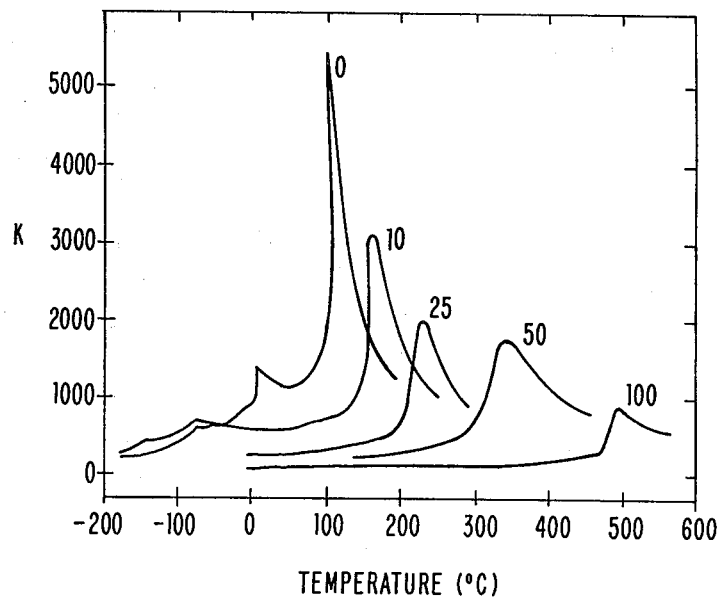
FIG. 4 is a graph showing dielectric constant as a function of temperature, with the percent of lead titanate in barium titanate as a variable.

Referring now to FIG. 1, there is shown in cutaway side view a surgical cutting instrument which has a blade-shaped element 9 that is suitably attached to a handle 11. An electrode 13 is disposed on one major face of the element 9 near the periphery thereof and another similar electrode 15 (not shown) is disposed on the opposite major face in approximate registration with electrode 13 on the one major face. These electrodes 13, 15 may be connected, respectively, to the terminals of a source 17 of radio frequency signal in such a manner that a radio frequency electric field is established within the element 9 between the electrodes 13, 15 in response to the radio frequency signal applied thereto. This causes local heating near the peripheral edges of the element 9 in the manner as previously described. And since the radio frequency electric field established between electrodes 13 and 15 independently affects the local regions of the dielectric, the operating temperatures of local regions may be regulated independently of the operating temperatures of adjacent regions. With a material which has the desirable characteristics previously discussed in connection with the graphs of FIGS. 3 and 4, and at the selected operating temperatures, the entire cutting edge can be maintained within a suitably constant temperature range despite the irregular and unpredictable manner in which the various regions of the cutting edge are used.

Figure 2:
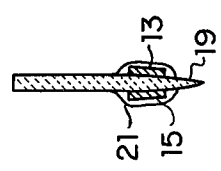
FIG. 2 is an end sectional view of one embodiment of a blade-shaped portion of an instrument as shown in FIG. 1.

The sectional view of FIG. 2 shows the arrangement of electrodes 13 and 15 disposed on opposite faces of the element 9 in approximate pattern registration adjacent the tissue-cutting edge of the element 9. An insulating material 21 such as silicon dioxide may be deposited on the major surfaces of element 9 and over the respective electrodes 13 and 15 to insulate the body of a patient from electrical signals appearing on these electrodes.

The radio frequency signal source 17 may be adjustable in signal amplitude or in frequency, or both, to adjust the ambient operating temperature of the cutting edge in air.

I claim:

1. A blade comprising a cutting means including a cutting edge having a dielectric means disposed in the region along said cutting edge, wherein said dielectric means includes a titanate composition of at least one of lead and barium; and electrode means disposed adjacent said dielectric means for establishing an electrical field through said dielectric means to dissipate power in response to an alternating electrical signal appearing on said electrode means.

2. A surgical instrument as in claim 1 wherein said dielectric means includes lead zirconate titanate.

3. A surgical blade for cutting tissue with simultaneous hemostasis, said blade comprising:

a cutting means including a cutting edge having a dielectric means disposed in the region along said cutting edge wherein said dielectric means includes a titanate composition; and electrode means for establishing an electrical field through said dielectric means in response to an electrical signal applied thereto.

4. A surgical blade claimed in claim 3 wherein said dielectric means includes lead zirconate titanate.

* * * * *